United States Patent [19]

Schwartz

[11] Patent Number: 4,952,583

[45] Date of Patent: Aug. 28, 1990

[54] AMINOPHENOL DERIVATIVES

[75] Inventor: John A. Schwartz, Macclesfield, United Kingdom

[73] Assignee: ICI Americas Inc., Wilmington, Del.

[21] Appl. No.: 354,540

[22] Filed: May 19, 1989

[30] Foreign Application Priority Data

May 25, 1988 [GB] United Kingdom ............... 8812343

[51] Int. Cl.$^5$ ................. A61K 31/495; C07D 241/16; C07D 241/20
[52] U.S. Cl. .................................. 514/225; 514/869; 544/407
[58] Field of Search ................ 544/407; 514/255, 869

[56] References Cited

U.S. PATENT DOCUMENTS

| | | | |
|---|---|---|---|
| 3,577,418 | 5/1971 | Crajoe et al. | 544/405 |
| 4,029,816 | 6/1977 | Crajoe et al. | 514/655 |
| 4,085,211 | 4/1978 | Crajoe, Jr. et al. | 514/255 |

*Primary Examiner*—Cecilia Shen
*Attorney, Agent, or Firm*—Thomas E. Jackson; James T. Jones

[57] ABSTRACT

Certain amine containing phenolic pyrazines of formula III possess eukalemic diuretic properties and are of value in treating diseases and conditions in which a eukalemic diuretic effect is required, for example in treating edema, hypertension and/or related conditions.

10 Claims, No Drawings

AMINOPHENOL DERIVATIVES

This invention comprises novel amine containing phenolic pyrazines which are useful as eukalemic diuretics.

A variety of agents are available for use in treating hypertension. One particular class of such agents is diuretics. Diuretics are used for a variety of purposes, for example, reduction of fluid from the body and reduction of sodium levels in the body, for example, in the treatment of hypertension and edema. An example of a diuretic is 2-(aminomethyl)-4-(1,1-dimethylethyl)-6-iodophenol hydrochloride of formula I (formula set out, together with other formulae referred to by Roman numberals, on pages following Examples) described in U.S. Pat. No. 4,029,816.

A problem with some diuretics is the reduction of serum potassium levels and complications caused from reductions of potassium beyond levels needed for maintaining physiological functions. Thus, some diuretics are used in conjunction with a potassium conserving agent such as 3,5-diamino-N-(aminoiminomethyl)-6-chloropyrazine carboxamide monohydrochloride, dihydrate of formula II described in U.S. Pat. No. 3,577,418 which is used in conjunction with, for example, thiazide diuretics.

There is thus a need for a single agent which is an effective but potassium-conserving (isokalemic, also called eukalemic) diuretic, such that it obviates the problems associated with hypokalemia (potassium depletion) and hyperkalemia (potassium buildup) without the need for taking multiple therapeutic agents.

A series of pyrazine-carboxamides has been described in U.S. Pat. No. 4,085,211 as eukalemic agents possessing diuretic and natriuretic properties. We have now discovered (and this is a basis for our invention) that, surprisingly, certain amine containing phenolic pyrazines of the formula III defined below possess eukalemic diuretic properties and are of value in treating those diseases and conditions in which a eukalemic diuretic effect is required, for example in treating edema, hypertension and/or related conditions.

SUMMARY OF THE INVENTION

The invention comprises compounds of formula III wherein: A is chloro or bromo: $R^4$ is hydrogen or (1-5-C)alkyl: $R^6$ is bromo, iodo or t-butyl; $R^7$ and $R^8$ are independently hydrogen, chloro, (1-5C)alkyl or (1-3C)alkoxy provided that when $R^6$ is bromo or iodo, then one or both of $R^7$ and $R^8$ are (1-3C)alkoxy; and Z is chloro, bromo, iodo, trifluoromethyl, methylsulfonyl or aminosulfonyl of formula $SO_2NR^{10}R^{11}$ wherein $R^{10}$ and $R^{11}$ are independently hydrogen or (1-5C)alkyl; and pharmaceutically acceptable salts thereof.

Particular values for $R^4$ when it is a (1-5C)alkyl group include methyl, ethyl and propyl.

Particular values for $R^7$ or $R^8$ when $R^7$ or $R^8$ is a (1-5C)alkyl group include methyl, ethyl and propyl; when $R^7$ or $R^8$ is a (1-3C)alkoxy group, particular values include methoxy and ethoxy.

Particular values for $R^{10}$ or $R^{11}$ when $R^{10}$ or $R^{11}$ is a (1-5C)alkyl group include methyl, ethyl and propyl.

More particular values for the groups and ranges described above include for example:
for A: chloro and bromo;
for $R^4$: hydrogen and (1-3C)alkyl;
for $R^6$: bromo and t-butyl;
for $R^7$ and $R^8$ (independently): hydrogen and methoxy; and
for Z: bromo and methylsulfonyl.

Preferred values for certain of the groups described above include, for example:
for A: chloro;
for $R^4$: methyl;
for $R^6$: t-butyl; and
for Z: bromo.

Preferred compounds include, for example:
(a) 3,5-diamino-N-[2-[[2-[[1-[3-bromo-5-(1,1-dimethylethyl)-2-hydroxyphenyl]ethyl]amino]-ethyl]methylamino]ethyl]-6-chloropyrazinecarboxamide; and
(b) 3,5-diamino-N-[2[[2-[[1-[3-bromo-5-(1,1-dimethylethyl)-2-hydroxy-4-methoxyphenyl]-ethyl]amino]ethyl]propylamino]ethyl]-6-chloropyrazinecarboxamide;
and the pharmaceutically acceptable salts thereof.

It will be appreciated that compounds of formula III, for example those containing an asymmetrically substituted carbon atom, may exist in, and be isolated in, optically-active and racemic forms. Some compounds may exhibit polymorphism. It is to be understood that the present invention encompasses any racemic, optically-active, tautomeric, polymorphic or stereoisomeric form, or mixtures thereof, which form possesses the properties described above, it being well known in the art how to prepare optically-active forms (for example, by resolution of the racemic form or by synthesis from optically-active starting materials) and how to establish the diuretic properties thereof (for example, by using one of the test procedures described herein).

It is to be understood that the generic term "(1-5C)alkyl" includes both straight and branched chain alkyl radicals but references to individual alkyl radicals such as "propyl" embrace only the straight chain ("normal") radical, branched chain isomers such as "isopropyl" being referred to specifically.

The compounds of the present invention may be prepared by methods which include processes known in the chemical art. Such processes for the manufacture of a compound of formula III as defined above are provided as further features of the invention and include the following procedures in which the meanings of the generic radicals are as defined above and "Pyz" has the structure shown in formula IV:

(A) Reductively alkylating a particular pyrazinamidoamine of formula VIII with an appropriate ketone of formula XI in a solvent such as ethanol or methanol by in situ formation of an intermediate imine of formula XII (which is formed but not isolated) and reduction with a reducing agent such as sodium borohydride or hydrogen and a catalyst. The desired reaction product is recovered by diluting the reaction mixture with water to precipitate the product, which may be purified by crystallization from an appropriate solvent, such as methanol or ethanol.

(B) Alkylation of a pyrazinamidoamine of formula VIII with a benzyl halide of formula XIV and, preferably, in the presence of a base such as, for example potassium carbonate or triethylamine, for example, for 1 to 5 days at, for example, room temperature. A solvent such as methanol or dimethylformamide is used. The desired reaction product is isolated by diluting the reaction mixture with water to precipitate the product, which may be purified by crystallization from an appropriate solvent, such as methanol or ethanol.

(C) Reacting a pyrazinamidoamine of formula VIII with a phenol of formula XV and acetaldehyde, such as, for example, by heating at temperatures up to 100° C. for 1 to 5 days. A solvent such as methanol or ethanol with an optional cosolvent such as tetrahydrofuran or dioxane is used. The desired reaction product is recovered by evaporation of the solvent and purified by crystallization from an alcohol such as ethanol.

(D) Acylating a benzylic triamine of formula XVI with a pyrazinoyl imidazole of formula V. The desired reaction product may be recovered by diluting the reaction mixture with water to precipitate the product, which may be purified by crystallization from an appropriate solvent, such as methanol or ethanol (E) Halogenating a selected phenolic pyrazine (corresponding to a compound of formula III with Z=hydrogen, prepared, for example, by analogy with method (A), (B), or (D) above) with a halogenating agent in a solvent such as acetic acid or methylene chloride. The desired product is recovered by evaporation of the solvent and crystallization from an appropriate solvent, such as methanol or ethanol (F) O-Dealkylating a selected alkyl aryl ether of formula XVIII, where $R^9$ is lower alkyl, for example, methyl (prepared, for example, by an analogous method to one described in method (A), (B) or (D) for compounds of formula III) with a dealkylating agent such as lithium thioethoxide or boron tribromide in a solvent such as dimethylformamide or methylene chloride respectively. The desired reaction product may be recovered by diluting the reaction mixture with water to precipitate the product, which may be purified by crystallization from an appropriate solvent, such as methanol or ethanol.

The benzylic triamines of formula XVI are prepared by mixing the particular aliphatic triamine of formula XIII (for selected aliphatic triamines see U.S. Pat. No. 3,201,472) with an appropriate ketone of formula XI in a solvent such as ethanol or methanol. The intermediate imines of formula XVII which are formed are not isolated but stirred with a reducing agent such as sodium borohydride or hydrogen and a catalyst. The desired reaction product is recovered by diluting the reaction mixture with water to precipitate the product, which may be purified by crystallization from a hydrocarbon solvent.

Pyrazinoic acids of formula $PyzCO_2H$ are prepared by the hydrolysis of the corresponding methyl esters of formula $PyzCO_2CH_3$. The hydrolysis is usually carried out using a solution of aqueous base such as sodium hydroxide and a solvent such as isopropanol or ethanol and stirring the mixture at room temperature for one to 24 hours. The pyrazinoic acid is then isolated by cooling and acidifying the mixture with an acid such as hydrochloric acid.

The pyrazinoyl imidazoles of formula V are prepared by reacting the corresponding acids of formula $PyzCO_2H$ with 1,1-carbonyldiimidazole (slight excess) in a solvent such as dimethylformamide or methanol at room temperature and stirring the mixture for 10 to 24 hours. The pyrazinoyl imidazoles are isolated by dilution with methanol or water.

The pyrazinamides of formula VI are prepared by mixing the particular pyrazinoyl imidazole with an aliphatic diamine of formula VII and stirring at ambient temperature for 5 to 24 hours. A solvent such as tetrahydrofuran may be added or an excess of the diamine may be used as the solvent. The desired reaction product is recovered by evaporating the solvent to provide the product which can be purified by crystallization from an alcohol such as ethanol.

Alternatively, pyrazinamides of formula VI may be prepared by mixing the particular pyrazinoic acid methyl ester with an excess of the aliphatic diamine of formula VII and heating at temperatures up to 100° C. for 1 to 24 hours. The desired reaction product is recovered by evaporation of the excess diamine.

Pyrazinamidoamines of formula VIII are prepared by mixing an aliphatic haloamine of formula IX where L is iodo, bromo or chloro and Q is a suitable amine protecting group, for example, a phthalimide or t-butyloxycarbonyl (BOC) such as in formula IXa, with the particular pyrazinamide of formula VI and a base such as potassium carbonate or triethylamine for 1 to 5 days at room temperature A solvent such as methanol or dimethylformamide is used. The protected pyrazinamidoamine of formula X is isolated by diluting with water It can be purified by recrystallization from an appropriate solvent such as ethanol. Removal of the protecting group provides the desired pyrazinamidoamine of formula VIII.

Alternatively, pyrazinamidoamines of formula VIII may be prepared by mixing the particular pyrazinoyl imidazolide with an excess of an aliphatic triamine of formula XIII in a solvent such as tetrahydrofuran. The desired reaction product is recovered by evaporating the solvent to provide the product Pharmaceutically acceptable salts may be obtained using standard procedures well known in the art, for example, by reacting a compound of formula III with a suitable acid affording a physiologically acceptable anion such as, for example, sulfuric acid, hydrochloric acid or citric acid As stated previously, the compounds of this invention or a salt thereof may be useful in the treatment of edema, hypertension and/or related conditions and particularly as diuretics, especially eukalemic diuretics. The compounds of formula III are also of value as pharmacological standards for the development and standardization of new disease models and assays for use in developing new therapeutic agents for treating hypertension.

When used in the treatment of one or more of the above mentioned diseases, a compound of formula III or a salt thereof may generally be administered as an appropriate pharmaceutical composition which comprises a compound of formula III as defined hereinbefore or a salt thereof together with a pharmaceutically acceptable diluent or carrier, the composition being adapted for the particular route of administration chosen. Such compositions are provided as a further feature of the invention They may be obtained by employing conventional procedures and excipients and binders and may be in a variety of dosage forms. For example, they may be in the form of tablets, capsules, solutions or suspensions for oral administration in the form of suppositories for rectal administration: in the form of sterile solutions or suspensions for administration by intravenous or intramuscular injection or infusion; and in the form of powders together with pharmaceutically acceptable inert solid diluents such as lactose For oral administration a tablet or capsule containing up to 250 mg (and typically 5 to 100 mg) of a compound of formula III or a salt thereof may conveniently be used Similarly, for intravenous or intramuscular injection or infusion a sterile solution or suspension containing up to 10% w/w (and typically 0.05 to 5% w/w) of a compound of formula III or a salt thereof may conveniently be used The dose of compound of formula III or a salt thereof to be administered will necessarily be varied according to principles well known in the art taking account of the route of administration and the severity of the condition and the size and age of the patient under treatment. However, in general, a compound of formula III or a salt thereof will be administered to a warm-blooded animal (such as man) so that a dose in the range of, for example, 0.05 to 25 mg/kg (and usually 0.5 to 10 mg/kg) is received.

The diuretic and eukalemic properties of a compound of formula III may be demonstrated by using standard tests.

TEST A.

Method:

Female Beagle dogs are selected from an established breeding colony (weight range 9.0–13.0 kg), placed on a special-diet of certified dog food and one can of Prescription Diet P/D Dog Food, and observed for suitability for training Dogs are selected from this group for training. Over a one to two week period the dogs are allowed to gradually build up tolerance to light restraint, standing, or sitting in a mesh sling support stand. Maximum time in sling is approximately 9 hours. Also, relaxed acceptance of the process of urinary bladder catheterization is accomplished during the training period Sterile Bardex foley catheters (sizes 8, 10 pediatric) are used. The conscious female Beagle dogs with free access to water are fasted overnight. The dogs are placed in sling support stands (Alice King Chatham) and catheterized. A short equilibration period of about 30 minutes allows time for residual urine to be drained fom the bladder. Urine spontaneously voided is collected in 50 ml pre-weighed tubes (Falcon). Two 1-hour control periods are followed by oral dosing with gelatin capsules containing test compounds or standard diuretics. Alternatively, some compounds are administered via oral gavage tubes in 10 ml quantities. No water loading is done. Spontaneously voided urine is collected for an additional six hours for a total collection period of eight hours. Afterward, dogs are returned to cages and fed and watered. Experiments are conducted once every two weeks on each dog, thus assuring adequate recovery between tests. Urine samples are weighed and measured for volume. Analysis of urinary electrolytes (sodium, potassium, chloride) is done on the following day. The analysis of urinary electrolytes showed results similar to other diuretics except that there was no excessive potassium loss.

TEST B:

Method

Beagle dogs obtained from the established breeding colony of Marshall Animal Facility or White Eagle Laboratories are utilized. Healthy male and/or female Beagles 9-13 kg in body weight are housed according to standard operating procedure (SOP) for Veterinary Services and are placed on a diet of "certified" dry dog food supplemented with one can of puppy diet P/D Prescription Diet dog food, with free access to water. A two-week minimum period of equilibration on this diet is necessary before determination of basal level electrolytes is attempted.

Prior to beginning actual drug dosing, six control blood samples are obtained to establish a range for basal level electrolytes. Control samples are evaluated for consistency in plasma K+ levels, and a range of less than 0.25 mEq of K+ is usually desirable. Historically, plasma K+ levels in the range of 4.00–4.30 mEq have been obtained. Any dog not approximating these values is normally dropped from the study.

Sampling Procedure

Plasma samples are obtained by forearm venopuncture via the saphenous vein or the jugular vein A 5 cc syringe with 20 gauge needle is used to obtain one 5 cc sample. The sample is preserved with 100 $\mu$l of 1000 unit heparin. Samples are centrifuged for ten minutes at 2500 rpm. Plasma is then pipetted into an appropriately labeled tube and all samples are frozen to await electrolytes determination.

Drug Dosing Schedule and Preparation:

After control samples are analyzed, the dogs are divided randomly into groups, allowing a minimum of four dogs per drug group. Test compounds are dosed on a mg/kg basis. Gelatin capsules size "2"00 and "3"000 are used. Alternatively, some compounds are administered via oral gavage tubes Compounds are suspended in 10 ml of saline by sonicating. The weight of the dog is determined by averaging the values over the three days of controls. Time of day for drug dosing is consistent throughout the study. Samples are required on days 4, 7, 11, 14, and 21, and 28. Dosing takes place midmorning (10 a.m. to 11 a.m.), and blood is drawn approximately three hours after dosing (1 p.m. to 2 p.m.). (Drug capsules are dosed orally followed by 5–10 cc of water from a syringe with oral dosing needle attached.) Hematocrits are taken with Microhematocrit capillary tubes and read immediately following collection of plasma samples

Data Evaluation:

Plasma samples are analyzed for potassium as described above and showed no substantial change in serum potassium.

In general, the compounds of this invention which were tested showed a profile as a eukalemic diuretic. Compounds of this invention which were tested have not shown any signs of overt toxicity following oral administration at a dose several multiples of the recommended therapeutic dose.

The invention will now be illustrated by the following non-limiting examples in which, unless stated otherwise:

(i) temperatures are given in degrees Celsius (C); operations were carried out at room or ambient temperature, that is, at a temperature in the range of 18°–25° C.;

(ii) evaporation of solvent was carried out using a rotary evaporator under reduced pressure (600–4000 pascals: 4.5–30 mm Hg) with a bath temperature of up to 60° C.;

(iii) flash chromatography was carried out on Merck Kieselgel (Art 9385) and column chromatography on Merck Kieselgel 60 (Art 7734): [these materials were obtained from E. Merck, Darmstadt, W. Germany] thin layer chromatography (TLC) was carried out on Analtech 0.25 mm silica gel GHLF plates (Art 21521), obtainable from Analtech, Newark, Del. U.S.A.

(iv) in general, the course of reactions was followed by TLC and reaction times are given for illustration only;

(v) melting points are uncorrected and (d) indicated decomposition; the melting points given are those obtained for the materials prepared as described; polymorphism may result in isolation of materials with different melting points in some preparations;

(vi) all final products were essentially pure by TLC and microanalytical data;

(vii) yields are given for illustration only;

(viii) reduced pressures are given as absolute pressures in pascals (Pa); other pressures are given as gauge pressures in bars;

(ix) chemical symbols have their usual meanings; the following abbreviations have also been used: v (volume), w (weight), mp (melting point), l [liter(s)], ml (milliliters), g [gram(s)], mg [milligram(s)];

(x) solvent ratios are given in volume: volume (v/v) terms;

(xi) TLC solvent systems: Solvent System A: 25:5:70 (v/v/v) methanol:triethylamine:methylene chloride;

(xii) some compounds are denoted by letters for Example (A), for later reference in the Examples; and (xiii) drying the organic phase was accomplished by swirling with sodium sulfate.

EXAMPLE 1

3,5-Diamino-N-[2-[[2-[[1-[3-bromo-5-(1,1-dimethylethyl)-2-hydroxyphenyl]ethyl]amino]ethyl]methylamino]ethyl]-6-chloropyrazinecarboxamide (Formula III, A=Cl, $R^4$=$CH_3$, $R^7$=$R^8$=H, Z=Br, $R^6$=$C(CH_3)_3$).

(a) A mixture of 2.87 g (10.0 mmol) of 3,5-diamino-N-[2-[(2-aminoethyl)methylamino]ethyl]-6-chloropyrazinecarboxamide (A) and 2.71 g (10.0 mmol) of 1-[3-bromo-5-(1,1-dimethylethyl)-2-hydroxyphenyl]ethanone (B) in 50 ml of methanol and 20 ml of methylene chloride was stirred at ambient temperature for 1 hour. Sodium borohydride (0.38 g, 10.0 mmol) was added. After 1 hour, the solvent was evaporated. The residue was partitioned between water and methylene chloride. The organic phase was dried and evaporated. The residue was chromatographed on silica gel (200 g) using 1:99 (v/v) methanol:methylene chloride as eluent. There was obtained 3.85 g (7.09 mmol, 71%) of the title compound as a white solid: mp 138°–139° C.

Analysis calculated for $C_{22}H_{33}BrClN_7O_2$: C, 48.67; H, 6.13; N, 18.06. Found: C, 48.60; H, 6.06; N, 17.75.

(b) A hydrochloride salt was prepared in ethanol: mp 209°–210° C.

Analysis calculated for $C_{22}H_{33}BrClN_7O_2 \cdot 2HCl$: C, 42.91; H, 5.73: N, 15.92. Found: C, 42.83; H, 5.64; N, 15.73.

(c) The starting material (A) was obtained as follows:

To a stirred solution of 84.0 g (0.744 mol) of N-(2-aminoethyl)-N-methyl-1,2-ethanediamine (see U.S. Pat. No. 3,201,472 as an example of how to obtain this material) in 700 ml of tetrahydrofuran was added 88.6 g (0.372 mol) of 1-(3,5-diamino-6-chloropyrazinoyl)imidazole (see U.S. Pat. No. 4,029,816 as an example of how to obtain this material) in 10 portions over 1.5 hours. After 1 hour at ambient temperature the reaction mixture was filtered and concentrated to 300 ml. The solution was added dropwise to 1.4 liters of ether with vigorous stirring. The solid was filtered, washed with ether and dried. There was obtained 74.3 g (0.258 mol, 70%) of 3,5-diamino-N-[2-[(2-aminoethyl)methylamino]ethyl]-6-chloropyrazinecarboxamide. A sample was filtered through a pad of silica gel and eluted with 5:95 (v/v) methanol:methylene chloride saturated with ammonia gas; mp 138°–139.5° C.

Analysis calculated for $C_{19}H_{18}ClN_7O$: C, 41.74; H, 6.31: N, 34.07. Found: C, 41.53; H, 6.15; N, 33.72.

(d) The starting material (B) was obtained as follows:

(1) A mixture of 12.86 g (50.0 mmol) of 2-hydroxy-3-bromo-5-(1,1-dimethylethyl)benzaldehyde (see L. C. Felton and J. H. Brewer, Science, 105:409 (1947) as an example of how to obtain this material) and 3.82 g (55.0 mmol) of hydroxylamine hydrochloride in 30 ml of ethanol, 30 ml of water and 30 ml of tetrahydrofuran was cooled in an ice-water bath. Sodium bicarbonate (5.04 g, 60.0 mmol) was added in small portions over 15 minutes. After stirring for 1 hour at ambient temperature, water (200 ml) was added and the solid was filtered and dried. There was obtained 13.2 g (78.5 mmol, 97%) of 2-hydroxy-3-bromo-5-(1,1-dimethylethyl)benzaldehyde oxime as a white solid; mp 167.5°–168° C.

Analysis calculated for $C_{11}H_{14}BrNO_2$: C, 48.55: H, 5.19; N, 5.15. Found: C, 48.33; H, 5.14; N, 4.93.

(2) A mixture of 12.0 g (44.0 mmol) of 2-hydroxy-3-bromo-5-(1,1-dimethylethyl)benzaldehyde oxime and 18.9 g (90.0 mmol) of trifluoroacetic anhydride in 100 ml of tetrahydrofuran was cooled in an ice-water bath. A solution of 15.2 g (150.0 mmol) of triethylamine in 40 ml of tetrahydrofuran was added. After refluxing overnight, the solvent was stripped. The residue was partitioned between water and methylene chloride. The organic phase was washed with 1N hydrochloric acid followed by saturated sodium bicarbonate, then dried and evaporated. The residue was crystallized from hexane to provide 10.4 g (41.2 mmol, 94%) of 2-hydroxy-3-bromo-5-(1,1 dimethylethyl)benzonitrile; mp 69°–71° C.

Analysis calculated for $C_{11}H_{12}BrNO$: C, 51.99: H, 4.76; N, 5.51. Found: C, 51.87; H, 4.77; N, 5.27.

(3) To a solution of 10.4 g (41.2 mmol) of 2-hydroxy-3-bromo-5-(1,1-dimethylethyl)benzonitrile in 50 ml of tetrahydrofuran was added 47 ml (133.9 mmol, 2.85M) methylmagnesium bromide in ether. After stirring overnight at ambient temperature, the reaction mixture was poured onto ice and made acidic with 2N hydrochloric acid. The aqueous solution was extracted with ether. The organic phase was dried and evaporated. Crystallization from 2-propanol gave 10.5 g (38.7 mmol, 94%) of 1-[3-bromo-5-(1,1-dimethylethyl)-2-hydroxyphenyl]ethanone: mp 98°–98.5° C.

Analysis calculated for $C_{12}H_{15}BrO_2$: C, 53.16; H, 5.58. Found: C, 53.19; H, 5.54.

EXAMPLES 2 AND 3

(a) The procedure described in Example 1 was repeated using 1-phenylethanones of formula XI to give products of formula III where A=Cl, $R^4$=$CH_3$, $R^6$=$C(CH_3)_3$ and $R^7$, $R^8$ and Z have the values shown Table I.

TABLE I

| Example | $R^7$ | $R^8$ | Z | mp °C. (Free Base) | % Yield | Salt Form | mp °C. Salt |
|---|---|---|---|---|---|---|---|
| 2 | H | Cl | Br | 155–156 | 74 | di-HCl | 177–179 |
| 3 | H | $OCH_3$ | Br | 144–146 | 51 | di-HCl | 147–149 |

(b) The 1-phenylethanone used in Example 2 was prepared as follows:

(1) A mixture of 50 0 g (0.39 mol) of 3-chlorophenol in 250 ml of hexane and 125 ml of 85% phosphoric acid was heated to reflux. A solution of 43.2 g (0.584 mol) of 2-methyl-2-propanol in 25 ml of hexane was added over 1 5 hours After addition, the reaction mixture was refluxed for 4 hours. The organic phase was separated and extracted four times with 30 ml of 1N sodium hydroxide solution The combined aqueous extracts were made acidic and extracted with methylene chloride The organic phase was dried and evaporated at 90° C. (0.33 bars). The residue was crystallized from hexane.

There was obtained 0.46 g (2.49 mmol, 0.6%) of 3-chloro-4-(1,1-dimethylethyl)phenol as a white solid after crystallization from hexane: mp 65°–67° C.

Analysis calculated for $C_{10}H_{13}ClO$: C, 65.04; H, 7.10. Found: C, 64.90; H, 6.89.

(2) A mixture of 9.65 g (52.2 mmol) of 3-chloro-4-(1,1-dimethylethyl)phenol and 7.37 g (52.2 mmol) of hexamethylenetetramine was refluxed in 150 ml of trifluoroacetic acid for 3 hours. The solution was cooled to ambient temperature and diluted with 500 ml of water. The aqueous residue was extracted with ether. The organic phase was washed with saturated sodium bicarbonate solution, dried and evaporated. The residue was chromatographed on 250 g of silica gel using a gradient from hexane to 20:80 (v/v) ether: hexane as eluent. There was obtained 1.87 g (8.79 mmol, 17%) of 2-hydroxy-4-chloro-5-(1,1-dimethylethyl)benzaldehyde; mp 38°–39° C.

Analysis calculated for: $C_{11}H_{13}ClO_2$: C, 62.12: H, 6.16. Found: C, 62.24; H, 6.18.

(3) A solution of 1.84 g (8.65 mmol) of 2-hydroxy-4-chloro-5-(1,1-dimethylethyl)benzaldehyde and 1.85 g (10.4 mmol) of N-bromosuccinimide in 30 ml of methylene chloride was stirred overnight at ambient temperature. The solvent was evaporated and the residue was partitioned between water and hexane. The organic phase was dried and evaporated. The residue was chromatographed on 150 g of silica gel using a gradient from 1:99 to 5:95 (v/v) of ether:hexane as eluent. There was obtained 2.05 g (7.03 mmol, 81%) of 2-hydroxy-3-bromo-4-chloro-5-(1,1-dimethylethyl)benzaldehyde after crystallization from hexane; mp 92°–94° C.

Analysis calculated for: $C_{11}H_{12}BrClO_2$: C, 45.31: H, 4.15. Found: C, 45.28; H, 4.10.

(4) A mixture of 2.25 g (7.72 mmol) of 2-hydroxy-3-bromo-4-chloro-5-(1,1-dimethylethyl)benzaldehyde and 0.59 g (8.49 mmol) of hydroxylamine hydrochloride in 15 ml of 1:1:1 tetrahydrofuran:ethanol:water was cooled in an ice-water bath. Sodium bicarbonate (0.78 g, 9.26 mmol) was added in small portions over 15 minutes. After stirring overnight at ambient temperature, water (25 ml) was added and the solid was filtered and dried. There was obtained 2.00 g (6.52 mmol, 85%) of 2-hydroxy-3-bromo-4-chloro-5-(1,1-dimethylethyl)benzaldehyde oxime as a white solid after crystallization from cyclohexane mp 175°–177° C.

Analysis calculated for: $C_{11}H_{13}BrClNO_2$: C, 43.09; H, 4.27; N, 4.57. Found: C, 43.21; H, 4.29; N, 4.52.

(5) A mixture of 2.20 g (7.18 mmol) of 2-hydroxy-3-bromo-4-chloro-5-(1,1-dimethylethyl)benzaldehyde oxime and 3.12 g (14.72 mmol) of trifluoroacetic anhydride in 15 ml of tetrahydrofuran was cooled in an ice-water bath. A solution of 2.18 g (21.54 mmol) of triethylamine in 10 ml of tetrahydrofuran was added After refluxing for 2 hours, the solvent was evaporated and the residue was partitioned between saturated aqueous sodium bicarbonate solution and ether. The organic phase was washed with 1N hydrochloric acid, followed by water and brine. The organic phase was dried and evaporated. The residue was chromatographed on 100 g of silica gel using a gradient from 5:95 to 50:50 (v/v) ether:hexane as eluent. There was obtained 1.80 g (6.23 mmol, 87%) of 2-hydroxy-3-bromo-4-chloro-5-(1,1-dimethylethyl)benzonitrile; mp 105°–107° C.

Analysis calculated for: $C_{11}H_{11}BrClNO$: C, 45.78; H, 3.84; N, 4.85. Found: C, 45.60; H, 3.88; N, 4.78.

(6) To a solution of 1.80 g (6.24 mmol) of 2-hydroxy-3-bromo-4-chloro-5-(1,1-dimethylethyl) benzonitrile in 30 ml of ether was added 5.20 ml (15.61 mmol, 3.0M) of methylmagnesium bromide in ether. After stirring overnight at ambient temperature, the reaction mixture was poured onto ice and made acidic with 2N hydrochloric acid. The aqueous solution was extracted with methylene chloride. The organic phase was dried and evaporated. Crystallization from 2-propanol gave 1 40 g (4.58 mmol, 74%) of 1-[3-bromo-4-chloro-5-(1,1-dimethylethyl)-2-hydroxyphenyl]ethanone mp 73°–74° C.

Analysis calculated for: $C_{12}H_{14}BrClO_2$: C, 47.16; H, 4.62. Found: C, 47.41; H, 4.56.

(c) The 1-phenylethanone used in Example 3 was prepared in the following manner:

(1) A solution of 10.0 g (51.5 mmol) of 1,3-dimethoxy-4-(1,1-dimethylethyl)benzene (see M. S. Carpenter et al, J. Org. Chem., 16:586 (195]) as an example of how to obtain this material) and 5.3 g (51.5 mmol) of acetic anhydride in 250 ml of methylene chloride was cooled in an ice-water bath. Tin (IV) chloride (6.02 ml, 51.5 mmol) was added dropwise over a five minute period. After addition, the reaction mixture was stirred for 15 minutes and poured onto ice. The aqueous phase was extracted with ether The organic phase was washed with saturated aqueous sodium bicarbonate solution, brine, and then dried and evaporated. The residue was crystallized from 2-propanol providing 11.3 g (47.9 mmol, 93%) of 1-[2,4-dimethoxy-5-(1,1-dimethylethyl)-phenyl]ethanone; mp 113°–115° C.

Analysis calculated for: $C_{14}H_{20}O_3$: C, 71 16; H, 8.53. Found: C, 71.04; H, 8.49.

(2) A solution of 12.2 g (51.5 mmol) of 1-[2,4-dimethoxy-5-(1,1-dimethylethyl)phenyl]ethanone in 250 ml of methylene chloride was cooled to −78° C. A solution of boron tribromide (51.5 ml, 51.5 mmol, 1M) in methylene chloride was added over 15 minutes. The reaction mixture was allowed to warm to ambient temperature over 1 hour. The reaction mixture was poured onto ice and the organic phase separated. The organic phase was washed with saturated aqueous sodium bicarbonate solution, dried and evaporated. The residue was crystallized from 2-propanol providing 11.2 g (50.3 mmol, 97%) of 1-[5-(1,1-dimethylethyl)-2-hydroxy-4-methoxyphenyl]ethanone; mp 85°–87° C.

Analysis calculated for: $C_{13}H_{18}O_3$: C, 70.25 H, 8.16. Found: C, 70.19; H, 8.05.

(3) To a solution of 10.7 g (48.1 mmol) of 1-[5-(1,1-dimethylethyl)-2-hydroxy-4-methoxyphenyl]ethanone in 250 ml of methylene chloride was added 8.11 g (50.7 mmol) of bromine. The reaction mixture was stirred at ambient temperature for 2 hours. Water (500 ml) was added. The organic phase was separated, washed with saturated aqueous sodium bicarbonate, dried and evaporated. The residue was filtered through 150 g of silica gel using 10:90 (v/v) ether:hexane as eluent. There was obtained 8.70 g (28.8 mmol, 60%) of 1-[3-bromo-5-(1,1-dimethylethyl)-2-hydroxy-4-methoxyphenyl]ethanone as white crystals after crystallization from hexane; mp 69°–71° C.

Analysis calculated for:

$C_{13}H_{17}BrO_3$: C, 51.84; H, 5.69. Found: C, 51.81; H, 5.63.

EXAMPLE 4

3,5-Diamino-N-[2-[[2-[[1-[3-bromo-5-(1,1-dimethylethyl)-2-hydroxyphenyl]ethyl]amino]ethyl]-propylamino]ethyl]-6-chloropyrazinecarboxamide (Formula III, A=Cl, $R^4$=$CH_2CH_2CH_3$, $R^7$=$R^8$=H, $R^6$=$C(CH_3)_3$, Z=Br).

(a) A mixture of 4.10 g (12.9 mmol) of 3,5-diamino-N-[2-[(2-aminoethyl)propylamino]ethyl]-6-chloropyrazinecarboxamide (C) and 3.50 g (12.9 mmol) of 1-[3-bromo-5-(1,1-dimethylethyl)-2-hydroxyphenyl]ethanone (B) in 120 ml of ethanol was stirred overnight at ambient temperature. Sodium borohydride (600 mg, 15.9 mmol) was added. After 1 hour the solvent was evaporated. The residue was partitioned between water and methylene chloride. The organic phase was dried and evaporated. The residue was chromatographed on silica gel (100 g) using 2:99 (v/v) methanol:methylene chloride as eluent. There was obtained 2.47 g (4.33 mmol, 33%) of the title compound as a white solid mp 134°–136° C.

Analysis calculated for: $C_{23}H_{37}BrClN_7O_2$: C, 50.49: H, 6.53; N, 17.17. Found: C, 50.57; H, 6.46; N, 17.16.

(b) A hydrochloride salt was prepared in ethanol; mp 167°–169° C.

Analysis calculated for: $C_{24}H_{37}BrClN_7O_2.2HCl.\frac{1}{2}H_2O$: C, 44.15: H, 6.18; N, 15.02. Found: C, 44.03; H, 5.74. N, 14.86.

(c) The starting material (C) was obtained as follows:

(1) A mixture of 118.6 g (1.67 mol) of acrylamide and 49.3 g (0.83 mmol) of 1-aminopropane in 250 ml of methanol was heated at 80° C. for 1 hour. The solvent was evaporated and the solid crystallized from ethanol. There was obtained 162.3 g (0.81 mol, 97%) of 3,3'-(propylimino)bispropanamide as a white solid mp 101°–101.5° C.

Analysis calculated for: $C_9H_{19}N_3O_2$: C, 53 71: H, 9.51; N, 20.88. Found: C, 53.94; H, 9.18; N, 20.77.

(2) To a solution of 2.3 liters of 5.25% sodium hypochlorite solution and 580 ml of 10N sodium hydroxide cooled in an ice water bath was added 162.3 g (0.81 mol) of 3,3'-(propylimino)bispropanamide dissolved in 75 ml of water. During the addition internal temperature was maintained at 5° C. The reaction mixture was then heated to 60° C. for 3 hours. The solution was cooled to ambient temperature and 1.084 Kg of sodium hydroxide was added. The aqueous solution was extracted with 2-propanol. The organic phase was dried and evaporated. The residue was fractionally distilled under high vacuum. There was obtained 72.5 g (0.49 mol, 60%) of N-(2-aminoethyl)-N-propyl-1,2-ethanediamine as a colorless liquid; bp 53°–57° C. at 266 Pascals. A sample was converted into an oxalate salt in methanol mp 171°–172° C.

Analysis calculated for: $C_7H_{19}N_3.3C_2H_2O_4$: C, 37.59; H, 6.07: N, 10.12. Found: C, 37.44; H, 6.11; N, 10.28.

(3) A mixture of 23.87 g (100.0 mmol) of 1-(3,5-diamino-6-chloropyrazinoyl)imidazole and 58.51 g (300.0 mmol) of N-(2-aminoethyl)-N-propyl-1,2-ethanediamine in 250 ml of tetrahydrofuran was stirred at ambient temperature overnight. The solvent and excess triamine were evaporated and the residue chromatographed on silica gel (150 g) using 1.5:98.5 (v/v) methanol:tetrahydrofuran saturated with ammonia gas as eluent. There was obtained 24.64 g (78.0 mmol, 78%) of 3,5-diamino-N-[2-[(2-aminoethyl)propylamino]ethyl]-6-chloropyrazinecarboxamide as a yellow solid; mp 91°–94° C.

Analysis calculated for: $C_{12}H_{22}ClN_7O.\frac{1}{4}CH_3OH$: C, 45.44: H, 7.16 N, 30.29. Found: C, 45.57; H, 6.91; N, 30.33.

EXAMPLE 5

3,5-Diamino-N-[2-[[2-[[1-[3-bromo-5-(1,1-dimethylethyl)-2-hydroxy-4-methoxyphenyl]ethyl]amino]ethyl]-propylamino]ethyl]-6-chloropyrazinecarboxamide (Formula III, A=Cl, $R^4$=$CH_2CH_2CH_3$, $R^7$=H, $R^8$=$OCH_3$, $R^6$=$C(CH_3)_3$, Z=Br).

(a) A mixture of 3.00 g (9.50 mmol) of 3,5-diamino-N-[2-[(2-aminoethyl)propylamino]ethyl]-6-chloropyrazinecarboxamide (C) and 2.00 g (6.64 mmol) of 1-[3-bromo-5-(1,1-dimethylethyl)-2-hydroxy-4-methoxyphenyl]ethanone (D) in 75 ml of ethanol was stirred overnight at ambient temperature. Sodium borohydride (300 mg, 7.97 mmol) was added. After 30 minutes the solvent was evaporated. The residue was partitioned between water and methylene chloride. The organic phase was dried and evaporated. The residue was chromatographed on silica gel (150 g) using 0.1:2:97.9 (v/v/v) of ammonium hydroxide:methanol:methylene chloride as eluent. There was obtained 1.49 g (2.48 mmol, 37%) of the title compound as a white solid; mp 93°–95° C.

Analysis calculated for: $C_{25}H_{39}BrClN_7O_3$: C, 49.96; H, 6.54: N, 16.31. Found C, 49.72; H, 6.45; N, 16.54.

(b) A hydrochloride salt was prepared in methanol: mp 165°–167° C.

Analysis calculated for $C_{25}H_{39}BrClN_7O_3.2HCl.0.5-H_2O$: C, 43.97: H, 6.20; N, 14.36. Found: C, 43.68; H, 5.86; N, 14.18.

(c) The amino starting material (C) was prepared as described in Example 4.

(d) The 1-phenylethanone (D) was prepared as described in Example 3.

EXAMPLE 6

| Capsule: Each capsule contains: | |
|---|---|
| Material | Quantity/350 mg Blend |
| Compound of Formula III | 120.0 mg. |
| Lactose, National Formulary (NF) Fast Flo | 175.0 mg. |
| Sodium starch glycolate, NF | 18.0 mg. |
| Pregelatinized starch, NF | 35.0 mg. |
| Magnesium stearate, NF | 2.0 mg. |

All of the above-listed materials, except the magnesium stearate, are screened through a suitable screen, for example, 20 mesh, and blended in a mixer for about 5 minutes The magnesium stearate is screened through a suitable screen, for example, 40 mesh, and the screened magnesium stearate is then added to the blended materials and mixed for 2 minutes. The blended powder is placed in a suitable and properly labeled container and encapsulated in two-piece hard gelatin capsules (size #0) as required.

FORMULAE
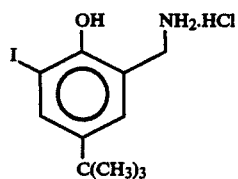 I
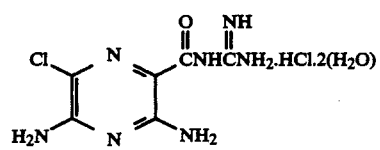 II
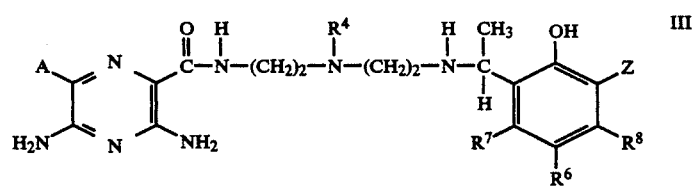 III
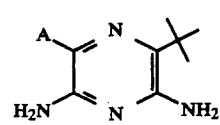 IV
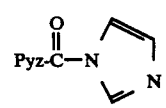 V
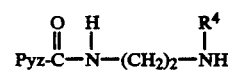 VI
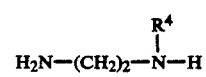 VII
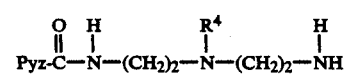 VIII
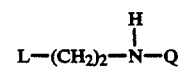 IX
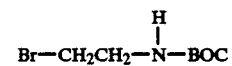 IXa
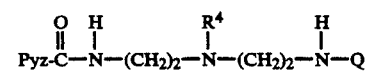 X
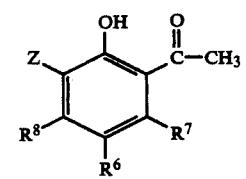 XI

FORMULAE
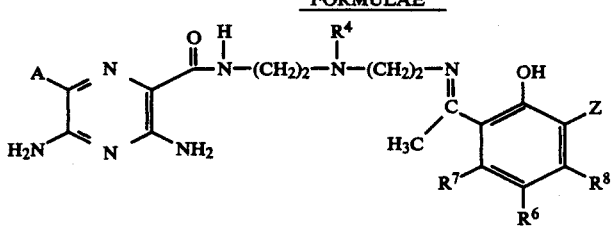  XII
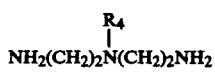  XIII
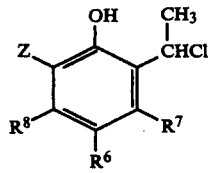  XIV
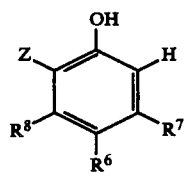  XV
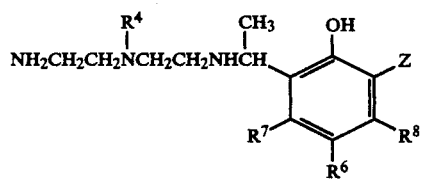  XVI
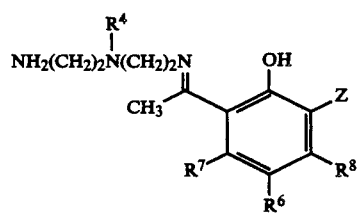  XVII
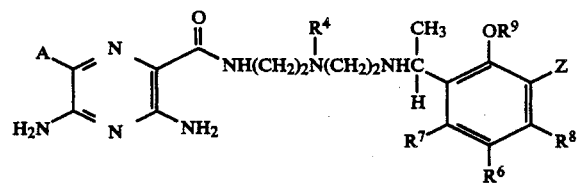  XVIII
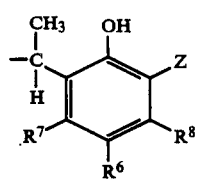
What is claimed is:
1. A compound having the formula
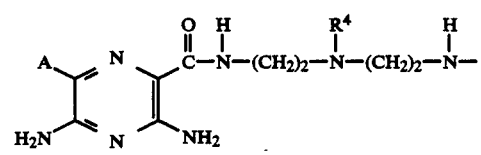  III
wherein:
A is chloro or bromo; $R^4$ is hydrogen or (1–5)alkyl; $R^6$ is bromo, iodo or t-butyl; $R^7$ and $R^8$ are independently hydrogen, chloro, (1–5C)alkyl or (1–3C)alkoxy provided that when $R^6$ is bromo or iodo, then one or both of $R^7$ and $R^8$ are (1–3C)alkoxy; and Z is chloro, bromo, iodo, trifluoromethyl, methylsulfonyl or aminosulfonyl of formula $SO_2NR^{10}R^{11}$ wherein $R^{10}$ and $R^{11}$ are independently hydrogen or (1–5C)alkyl;

or a pharmaceutically acceptable salt thereof.

2. A compound as claimed in claim 1, wherein $R^4$ is hydrogen, methyl, ethyl, or propyl: $R^7$ and $R^8$ are, independently, hydrogen, chloro, methyl, ethyl, propyl, methoxy or ethoxy, provided that when $R^6$ is bromo or iodo, then one or both of $R^7$ and $R^8$ are methoxy or ethoxy: and $R^{10}$ and $R^{11}$ are independently hydrogen, methyl, ethyl or propyl.

3. A compound as claimed in claim 1, wherein $R^4$ is hydrogen or (1–3C)alkyl: $R^6$ is bromo or t-butyl; $R^7$ and $R^8$ are, independently, hydrogen or methoxy and Z is bromo or methylsulfonyl.

4. A compound as claimed in claim 3, wherein A is chloro: $R^4$ is methyl, $R^6$ is t-butyl, and Z is bromo.

5. A compound as claimed in claim 1, which is 3,5-diamino-N-[2-[[2-[[1-[3-bromo-5-(1,1-dimethylethyl)-2-hydroxyphenyl]ethyl]amino]ethyl]methylamino]-ethyl]- 6-chloropyrazinecarboxamide, and pharmaceutically acceptable salts thereof.

6. A compound as claimed in claim 1, which is 3,5-diamino-N-[2[[2-[[1-[3-bromo-5-(1,1-dimethylethyl)-2-hydroxy-4-methoxyphenyl]ethyl]amino]ethyl]-propylamino]ethyl]-6-chloropyrazinecarboxamide, and pharmaceutically acceptable salts thereof.

7. A pharmaceutical composition comprising a eukalemic diuretic amount of a compound of claim 1 or a pharmaceutically acceptable salt thereof and a pharmaceutically acceptable diluent or carrier.

8. A composition as claimed in claim 7, in the form of a tablet, capsule, solution, suspension, suppository, injectable, or powder.

9. A method of inducing eukalemic diuresis in a mammal comprising administering to said mammal a pharmaceutically effective amount of a compound of claim 1 or a pharmaceutically acceptable salt thereof.

10. A method of treating hypertension in a mammal comprising administering a pharmaceutically effective amount of a compound of claim 1 or a pharmaceutically acceptable salt thereof to mammal in need of such treatment.

* * * * *